United States Patent
Buan et al.

(10) Patent No.: US 10,300,178 B2
(45) Date of Patent: May 28, 2019

(54) METHOD FOR PROVIDING NEGATIVE PRESSURE TO A NEGATIVE PRESSURE WOUND THERAPY BANDAGE

(71) Applicant: Smith & Nephew, Inc., Memphis, TN (US)

(72) Inventors: John Buan, Maple Grove, MN (US); Richard Willems, Big Lake, MN (US)

(73) Assignee: Smith & Nephew, Inc., Memphis, TN (US)

( * ) Notice: Subject to any disclaimer, the term of this patent is extended or adjusted under 35 U.S.C. 154(b) by 694 days.

(21) Appl. No.: 14/737,387

(22) Filed: Jun. 11, 2015

(65) Prior Publication Data
US 2015/0352267 A1    Dec. 10, 2015

Related U.S. Application Data

(63) Continuation of application No. 13/299,783, filed on Nov. 18, 2011, now Pat. No. 9,067,003.

(60) Provisional application No. 61/490,118, filed on May 26, 2011.

(51) Int. Cl.
*A61F 13/00*    (2006.01)
*A61M 1/00*    (2006.01)

(52) U.S. Cl.
CPC ..... *A61M 1/0031* (2013.01); *A61F 13/00068* (2013.01); *A61M 1/0037* (2013.01); *A61M 1/0088* (2013.01); *A61F 2013/00174* (2013.01); *A61F 2013/00536* (2013.01); *A61M 2205/33* (2013.01); *A61M 2210/04* (2013.01)

(58) Field of Classification Search
CPC .... A61F 13/00068; A61F 2013/00536; A61M 1/0031; A61M 1/0037; A61M 2205/33
See application file for complete search history.

(56) References Cited

U.S. PATENT DOCUMENTS

| | | | |
|---|---|---|---|
| 695,270 | A | 3/1902 | Beringer |
| 1,480,562 | A | 1/1924 | Mock |
| 2,280,915 | A | 4/1942 | Johnson |
| 2,367,690 | A | 1/1945 | Purdy |
| 2,568,933 | A | 9/1951 | Robbins |
| 2,632,443 | A | 3/1953 | Lesher |
| 2,682,873 | A | 7/1954 | Evans et al. |
| 3,367,332 | A | 2/1968 | Groves |
| 3,486,504 | A | 12/1969 | Austin et al. |

(Continued)

FOREIGN PATENT DOCUMENTS

| | | |
|---|---|---|
| CA | 2198243 A1 | 2/1996 |
| CA | 2367460 A1 | 10/2000 |

(Continued)

OTHER PUBLICATIONS

US 6,306,115, 10/2001, Kelly et al. (withdrawn)

(Continued)

*Primary Examiner* — Kai H Weng
(74) *Attorney, Agent, or Firm* — Knobbe, Martens, Olson & Bear LLP

(57) ABSTRACT

A method for providing a negative pressure wherein a pump is cycled on and off to achieve a target negative pressure, which is set slightly lower than the therapeutic negative pressure. A device determines the actual pressure by averaging samples which may occur at a different rate than the pump cycle.

27 Claims, 3 Drawing Sheets

(56) References Cited

U.S. PATENT DOCUMENTS

| | | |
|---|---|---|
| 3,572,340 A | 3/1971 | Lloyd et al. |
| 3,610,238 A | 10/1971 | Rich et al. |
| 3,874,387 A | 4/1975 | Barbieri |
| 3,993,080 A | 11/1976 | Loseff |
| RE29,319 E | 7/1977 | Nordby |
| 4,062,012 A | 12/1977 | Colbert et al. |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,250,882 A | 2/1981 | Adair |
| 4,316,466 A | 2/1982 | Babb |
| 4,382,441 A | 5/1983 | Svedman |
| 4,465,485 A | 8/1984 | Kashmer et al. |
| 4,468,227 A | 8/1984 | Jensen |
| 4,525,166 A | 6/1985 | Laclerc |
| 4,534,356 A | 8/1985 | Papadakis |
| 4,551,141 A | 11/1985 | McNeil |
| 4,573,965 A | 3/1986 | Russo |
| 4,608,041 A | 8/1986 | Nielsen |
| 4,643,641 A | 2/1987 | Clausen et al. |
| 4,655,766 A | 4/1987 | Theeuwes et al. |
| 4,681,562 A | 7/1987 | Beck et al. |
| 4,710,165 A | 12/1987 | McNeil et al. |
| 4,778,446 A | 10/1988 | Jensen |
| 4,778,456 A | 10/1988 | Lokken |
| 4,792,328 A | 12/1988 | Beck et al. |
| 4,795,435 A | 1/1989 | Steer |
| 4,820,284 A | 4/1989 | Hauri |
| 4,921,488 A | 5/1990 | Maitz et al. |
| 4,936,834 A | 6/1990 | Beck et al. |
| 4,950,483 A | 8/1990 | Ksander et al. |
| 4,969,880 A | 11/1990 | Zamierowski |
| 4,972,829 A | 11/1990 | Knerr |
| 4,979,944 A | 12/1990 | Luzsicza |
| 4,994,022 A | 2/1991 | Steffler et al. |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,127,388 A | 7/1992 | Cicalese et al. |
| 5,149,331 A | 9/1992 | Ferdman et al. |
| 5,152,757 A | 10/1992 | Eriksson |
| 5,167,613 A | 12/1992 | Karami et al. |
| 5,176,663 A | 1/1993 | Svedman et al. |
| 5,215,519 A | 6/1993 | Shettigar |
| 5,261,893 A | 11/1993 | Zamierowski |
| 5,266,928 A | 11/1993 | Johnson |
| 5,279,608 A | 1/1994 | Cherif Cheikh |
| 5,328,614 A | 7/1994 | Matsumura |
| 5,358,494 A | 10/1994 | Svedman |
| 5,380,280 A | 1/1995 | Peterson |
| 5,437,651 A | 8/1995 | Todd et al. |
| 5,445,604 A | 8/1995 | Lang |
| 5,489,280 A | 2/1996 | Russell |
| 5,498,338 A | 3/1996 | Kruger et al. |
| 5,527,293 A | 6/1996 | Zamierowski |
| 5,549,584 A | 8/1996 | Gross |
| 5,562,107 A | 10/1996 | Lavender et al. |
| 5,616,121 A | 4/1997 | McKay |
| 5,636,643 A | 6/1997 | Argenta et al. |
| 5,643,189 A | 7/1997 | Masini |
| 5,645,081 A | 7/1997 | Argenta et al. |
| 5,678,564 A | 10/1997 | Lawrence et al. |
| 5,733,337 A | 3/1998 | Carr et al. |
| 5,759,570 A | 6/1998 | Arnold |
| 5,785,688 A | 7/1998 | Joshi et al. |
| 5,830,496 A | 11/1998 | Freeman |
| 5,833,646 A | 11/1998 | Masini |
| 5,843,011 A | 12/1998 | Lucas |
| 5,857,502 A | 1/1999 | Buchalter |
| 5,868,933 A | 2/1999 | Patrick et al. |
| 5,876,611 A | 3/1999 | Shettigar |
| 5,964,723 A | 10/1999 | Augustine |
| 6,071,267 A | 6/2000 | Zamierowski |
| 6,103,951 A | 8/2000 | Freeman |
| 6,110,197 A | 8/2000 | Augustine et al. |
| 6,135,116 A | 10/2000 | Vogel et al. |
| D434,150 S | 11/2000 | Turney et al. |
| 6,142,982 A | 11/2000 | Hunt et al. |
| 6,168,800 B1 | 1/2001 | Dobos et al. |
| 6,176,307 B1 | 1/2001 | Danos et al. |
| 6,225,523 B1 | 5/2001 | Masini |
| 6,254,567 B1 | 7/2001 | Treu et al. |
| 6,255,552 B1 | 7/2001 | Cummings et al. |
| 6,261,283 B1 | 7/2001 | Morgan et al. |
| 6,287,521 B1 | 9/2001 | Quay et al. |
| 6,345,623 B1 | 2/2002 | Heaton et al. |
| 6,398,767 B1 | 6/2002 | Fleischmann |
| 6,402,724 B1 | 6/2002 | Smith et al. |
| 6,450,773 B1 | 9/2002 | Upton |
| 6,458,109 B1 | 10/2002 | Henley et al. |
| 6,465,708 B1 | 10/2002 | Augustine |
| 6,471,685 B1 | 10/2002 | Johnson |
| 6,471,982 B1 | 10/2002 | Lydon et al. |
| 6,482,491 B1 | 11/2002 | Samuelsen et al. |
| 6,491,684 B1 | 12/2002 | Joshi et al. |
| 6,553,998 B2 | 4/2003 | Heaton et al. |
| 6,599,262 B1 | 7/2003 | Masini |
| 6,648,862 B2 | 11/2003 | Watson |
| 6,673,028 B1 | 1/2004 | Argenta et al. |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,756,903 B2 | 6/2004 | Omry et al. |
| 6,764,462 B2 | 7/2004 | Risk, Jr. et al. |
| 6,767,334 B1 | 7/2004 | Randolph |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb |
| 6,951,553 B2 | 10/2005 | Bubb et al. |
| 6,977,323 B1 | 12/2005 | Swenson |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,118,545 B2 | 10/2006 | Boyde |
| 7,128,735 B2 | 10/2006 | Weston |
| 7,195,624 B2 | 3/2007 | Lockwood |
| 7,214,202 B1 | 5/2007 | Vogel et al. |
| 7,216,651 B2 | 5/2007 | Argenta et al. |
| 7,361,184 B2 | 4/2008 | Joshi |
| 7,381,859 B2 | 6/2008 | Hunt et al. |
| 7,438,705 B2 | 10/2008 | Karpowicz et al. |
| 7,494,482 B2 | 2/2009 | Orgill et al. |
| 7,503,910 B2 | 3/2009 | Adahan |
| 7,524,315 B2 | 4/2009 | Blott et al. |
| 7,534,240 B1 | 5/2009 | Johnson |
| 7,534,927 B2 | 5/2009 | Lockwood |
| 7,569,742 B2 | 8/2009 | Haggstrom |
| 7,611,500 B1 | 11/2009 | Lina et al. |
| 7,612,247 B2 | 11/2009 | Oyaski |
| 7,615,036 B2 | 11/2009 | Joshi |
| 7,645,253 B2 | 1/2010 | Gura et al. |
| 7,645,269 B2 | 1/2010 | Zamierowski |
| 7,678,090 B2 | 3/2010 | Risk, Jr. |
| 7,699,823 B2 | 4/2010 | Haggstrom |
| 7,699,830 B2 | 4/2010 | Martin |
| 7,708,724 B2 | 5/2010 | Weston |
| 7,717,313 B2 | 5/2010 | Criscuolo et al. |
| 7,753,894 B2 | 7/2010 | Blott et al. |

(56) References Cited

U.S. PATENT DOCUMENTS

| | | |
|---|---|---|
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. |
| 7,775,998 B2 | 8/2010 | Riesinger |
| 7,776,028 B2 | 8/2010 | Miller et al. |
| 7,779,625 B2 | 8/2010 | Joshi |
| 7,790,945 B1 | 9/2010 | Watson, Jr. |
| 7,790,946 B2 | 9/2010 | Mulligan |
| 7,794,438 B2 | 9/2010 | Henley |
| 7,794,450 B2 | 9/2010 | Blott et al. |
| 7,811,269 B2 | 10/2010 | Boynton |
| 7,815,616 B2 | 10/2010 | Boehringer et al. |
| 7,825,289 B2 | 11/2010 | Vess |
| 7,828,782 B2 | 11/2010 | Suzuki |
| 7,838,717 B2 | 11/2010 | Haggstrom |
| 7,846,141 B2 | 12/2010 | Weston |
| 7,862,339 B2 | 1/2011 | Mulligan |
| 7,883,494 B2 | 2/2011 | Martin |
| 7,909,805 B2 | 3/2011 | Weston |
| 7,927,319 B2 | 4/2011 | Lawhorn |
| 7,959,624 B2 | 6/2011 | Riesinger |
| 7,964,766 B2 | 6/2011 | Blott et al. |
| 7,976,519 B2 | 7/2011 | Bubb et al. |
| 7,998,125 B2 | 8/2011 | Weston |
| 8,025,052 B2 | 9/2011 | Matthews et al. |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston |
| 8,105,295 B2 | 1/2012 | Blott et al. |
| 8,118,794 B2 | 2/2012 | Weston |
| 8,128,615 B2 | 3/2012 | Blott |
| 8,152,785 B2 | 4/2012 | Vitaris |
| 8,162,907 B2 | 4/2012 | Heagle |
| 8,162,909 B2 | 4/2012 | Blott et al. |
| 8,167,869 B2 | 5/2012 | Wudyka |
| 8,235,955 B2 | 8/2012 | Blott et al. |
| 8,241,018 B2 | 8/2012 | Harr |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,353,857 B2 | 1/2013 | Rosenberg |
| 8,366,692 B2 | 2/2013 | Weston |
| 8,377,016 B2 | 2/2013 | Argenta et al. |
| 8,398,614 B2 | 3/2013 | Blott |
| D679,819 S | 4/2013 | Peron |
| D679,820 S | 4/2013 | Peron |
| 8,444,392 B2 | 5/2013 | Turner et al. |
| 8,449,509 B2 | 5/2013 | Weston |
| 8,460,255 B2 | 6/2013 | Joshi et al. |
| 8,494,349 B2 | 7/2013 | Gordon |
| 8,617,129 B2 | 12/2013 | Hartwell |
| 8,641,693 B2 | 2/2014 | Locke et al. |
| 8,663,198 B2 | 3/2014 | Buan et al. |
| 8,663,200 B2 | 3/2014 | Weston et al. |
| 8,715,256 B2 | 5/2014 | Greener |
| 8,734,425 B2 | 5/2014 | Nicolini |
| 8,764,732 B2 | 7/2014 | Hartwell |
| 8,785,059 B2 | 7/2014 | Hartwell |
| 8,795,243 B2 | 8/2014 | Weston |
| 8,808,259 B2 | 8/2014 | Walton et al. |
| 8,808,274 B2 | 8/2014 | Hartwell |
| 8,814,841 B2 | 8/2014 | Hartwell |
| 8,834,451 B2 | 9/2014 | Blott et al. |
| 8,905,985 B2 | 12/2014 | Allen et al. |
| 8,945,074 B2 | 2/2015 | Buan et al. |
| 8,951,235 B2 | 2/2015 | Allen et al. |
| 9,084,845 B2 | 7/2015 | Adie et al. |
| 2001/0016205 A1 | 8/2001 | Shimizu |
| 2001/0029956 A1 | 10/2001 | Argenta |
| 2001/0034499 A1 | 10/2001 | Sessions et al. |
| 2002/0065494 A1 | 5/2002 | Lockwood et al. |
| 2002/0068913 A1 | 6/2002 | Fleischmann |
| 2002/0115952 A1 | 8/2002 | Tumey |
| 2002/0120185 A1 | 8/2002 | Johnson |
| 2002/0143286 A1 | 10/2002 | Tumey |
| 2002/0150720 A1 | 10/2002 | Howard et al. |
| 2002/0161346 A1 | 10/2002 | Lockwood et al. NUM |
| 2002/0183702 A1 | 12/2002 | Henley et al. |
| 2002/0198503 A1 | 12/2002 | Risk et al. |
| 2002/0198504 A1 | 12/2002 | Risk et al. |
| 2003/0014022 A1 | 1/2003 | Lockwood et al. |
| 2003/0014025 A1 | 1/2003 | Allen et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0088202 A1 | 5/2003 | Gilman |
| 2003/0097086 A1 | 5/2003 | Gura |
| 2003/0108587 A1 | 6/2003 | Orgill et al. |
| 2003/0125649 A1 | 7/2003 | McIntosh |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0208149 A1 | 11/2003 | Coffey |
| 2003/0212357 A1 | 11/2003 | Pace |
| 2003/0212431 A1 | 11/2003 | Brady et al. |
| 2003/0225347 A1 | 12/2003 | Argenta et al. |
| 2004/0019342 A1 | 1/2004 | Nagasuna et al. |
| 2004/0030304 A1 | 2/2004 | Hunt et al. |
| 2004/0039391 A1 | 2/2004 | Argenta et al. |
| 2004/0039415 A1 | 2/2004 | Zamierowski |
| 2004/0054338 A1 | 3/2004 | Bybordi et al. |
| 2004/0064132 A1 | 4/2004 | Boehringer et al. |
| 2004/0118460 A1* | 6/2004 | Stinson ............... A61M 1/0031 137/557 |
| 2004/0122434 A1 | 6/2004 | Argenta et al. |
| 2004/0127834 A1 | 7/2004 | Sigurjonsson et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0225208 A1 | 11/2004 | Johnson |
| 2004/0241214 A1 | 12/2004 | Kirkwood et al. |
| 2004/0249353 A1 | 12/2004 | Risk, Jr. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0028828 A1 | 2/2005 | Heaton et al. |
| 2005/0033214 A1 | 2/2005 | Cantor |
| 2005/0058694 A1 | 3/2005 | Nielsen |
| 2005/0070835 A1 | 3/2005 | Joshi |
| 2005/0080372 A1 | 4/2005 | Nielsen et al. |
| 2005/0090787 A1 | 4/2005 | Risk, Jr. |
| 2005/0148913 A1 | 7/2005 | Weston |
| 2005/0222527 A1 | 10/2005 | Miller et al. |
| 2005/0261643 A1 | 11/2005 | Bybordi et al. |
| 2005/0267402 A1 | 12/2005 | Stewart et al. |
| 2006/0015087 A1 | 1/2006 | Risk, Jr. et al. |
| 2006/0025727 A1 | 2/2006 | Boehringer et al. |
| 2006/0029650 A1 | 2/2006 | Coffey |
| 2006/0041247 A1 | 2/2006 | Petrosenko et al. |
| 2006/0069365 A1 | 3/2006 | Sperl et al. |
| 2006/0079852 A1 | 4/2006 | Bubb et al. |
| 2006/0083623 A1 | 4/2006 | Higgins et al. |
| 2006/0100586 A1 | 5/2006 | Karpowicz et al. |
| 2006/0100594 A1 | 5/2006 | Adams et al. |
| 2006/0116620 A1 | 6/2006 | Oyaski |
| 2006/0129137 A1 | 6/2006 | Lockwood |
| 2006/0149170 A1 | 7/2006 | Boynton et al. |
| 2006/0282175 A1 | 12/2006 | Haines et al. |
| 2007/0005028 A1 | 1/2007 | Risk, Jr. |
| 2007/0010797 A1 | 1/2007 | Nishtala et al. |
| 2007/0032762 A1 | 2/2007 | Vogel |
| 2007/0038172 A1 | 2/2007 | Zamierowski |
| 2007/0055209 A1 | 3/2007 | Patel et al. |
| 2007/0118096 A1 | 5/2007 | Smith et al. |
| 2007/0141128 A1 | 6/2007 | Blott et al. |
| 2007/0167884 A1 | 7/2007 | Mangrum et al. |
| 2007/0179460 A1 | 8/2007 | Adahan |
| 2007/0185426 A1 | 8/2007 | Ambrosio et al. |
| 2007/0185463 A1 | 8/2007 | Mulligan |

(56) References Cited

U.S. PATENT DOCUMENTS

| | | |
|---|---|---|
| 2007/0219532 A1 | 9/2007 | Karpowicz et al. |
| 2007/0239139 A1 | 10/2007 | Weston |
| 2007/0265585 A1 | 11/2007 | Joshi et al. |
| 2007/0265586 A1 | 11/2007 | Joshi |
| 2008/0004549 A1 | 1/2008 | Anderson |
| 2008/0004559 A1 | 1/2008 | Riesinger |
| 2008/0039759 A1 | 2/2008 | Holm et al. |
| 2008/0077091 A1 | 3/2008 | Mulligan |
| 2008/0082059 A1 | 4/2008 | Fink |
| 2008/0108977 A1 | 5/2008 | Heaton et al. |
| 2008/0119802 A1 | 5/2008 | Riesinger |
| 2008/0167593 A1 | 7/2008 | Fleischmann |
| 2008/0183119 A1 | 7/2008 | Joshi |
| 2008/0188820 A1 | 8/2008 | Joshi |
| 2008/0208147 A1 | 8/2008 | Argenta et al. |
| 2008/0223378 A1 | 9/2008 | Henderson et al. |
| 2008/0269651 A1 | 10/2008 | Warlick et al. |
| 2008/0306407 A1 | 12/2008 | Taylor |
| 2008/0306456 A1 | 12/2008 | Riesinger |
| 2009/0005746 A1 | 1/2009 | Nielsen |
| 2009/0012441 A1 | 1/2009 | Mulligan |
| 2009/0030402 A1 | 1/2009 | Adahan |
| 2009/0036873 A1 | 2/2009 | Nielsen |
| 2009/0054855 A1 | 2/2009 | Blott et al. |
| 2009/0054856 A1 | 2/2009 | Mormino et al. |
| 2009/0069759 A1 | 3/2009 | Blott et al. |
| 2009/0105670 A1 | 4/2009 | Bentley et al. |
| 2009/0125004 A1 | 5/2009 | Shen |
| 2009/0131888 A1 | 5/2009 | Joshi |
| 2009/0177135 A1 | 7/2009 | Rogers et al. |
| 2009/0192499 A1 | 7/2009 | Weston et al. |
| 2009/0198201 A1 | 8/2009 | Adahan |
| 2009/0216170 A1 | 8/2009 | Robinson et al. |
| 2009/0221977 A1 | 9/2009 | Blott et al. |
| 2009/0227968 A1 | 9/2009 | Vess |
| 2009/0227969 A1 | 9/2009 | Jaeb |
| 2009/0234306 A1 | 9/2009 | Vitaris |
| 2009/0234307 A1 | 9/2009 | Vitaris |
| 2009/0234309 A1 | 9/2009 | Vitaris et al. |
| 2009/0240185 A1 | 9/2009 | Jaeb et al. |
| 2009/0240218 A1 | 9/2009 | Braga et al. |
| 2009/0254053 A1 | 10/2009 | Svensby |
| 2009/0254054 A1 | 10/2009 | Blott et al. |
| 2009/0264837 A1 | 10/2009 | Adahan |
| 2009/0270820 A1 | 10/2009 | Johnson |
| 2009/0270833 A1 | 10/2009 | DeBelser et al. |
| 2009/0292264 A1 | 11/2009 | Hudspeth et al. |
| 2009/0299251 A1 | 12/2009 | Buan |
| 2009/0299255 A1 | 12/2009 | Kazala, Jr. et al. |
| 2009/0299256 A1 | 12/2009 | Barta et al. |
| 2009/0299257 A1 | 12/2009 | Long et al. |
| 2009/0299306 A1 | 12/2009 | Buan |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0306580 A1 | 12/2009 | Blott et al. |
| 2009/0312723 A1 | 12/2009 | Blott et al. |
| 2009/0312728 A1 | 12/2009 | Randolph et al. |
| 2009/0326487 A1 | 12/2009 | Vitaris |
| 2010/0010477 A1 | 1/2010 | Augustine et al. |
| 2010/0036334 A1 | 2/2010 | Heagle et al. |
| 2010/0036367 A1 | 2/2010 | Krohn |
| 2010/0042074 A1 | 2/2010 | Weston |
| 2010/0063483 A1 | 3/2010 | Adahan |
| 2010/0063484 A1 | 3/2010 | Heagle |
| 2010/0069858 A1 | 3/2010 | Olson |
| 2010/0069863 A1 | 3/2010 | Olson |
| 2010/0087767 A1 | 4/2010 | McNeil |
| 2010/0100063 A1 | 4/2010 | Joshi et al. |
| 2010/0100075 A1 | 4/2010 | Weston et al. |
| 2010/0106114 A1 | 4/2010 | Weston et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0126484 A1 | 5/2010 | Skell et al. |
| 2010/0150991 A1 | 6/2010 | Bernstein |
| 2010/0160879 A1 | 6/2010 | Weston |
| 2010/0160880 A1 | 6/2010 | Weston |
| 2010/0185163 A1 | 7/2010 | Heagle |
| 2010/0185165 A1 | 7/2010 | Middleton |
| 2010/0207768 A1 | 8/2010 | Pidgeon |
| 2010/0249733 A9 | 9/2010 | Blott et al. |
| 2010/0268198 A1 | 10/2010 | Buan et al. |
| 2010/0274207 A1 | 10/2010 | Weston |
| 2010/0278518 A1* | 11/2010 | Gordon ............... A61M 1/0031 388/811 |
| 2010/0280468 A1 | 11/2010 | Haggstrom et al. |
| 2010/0286635 A1 | 11/2010 | Watson, Jr. |
| 2010/0286638 A1 | 11/2010 | Malhi |
| 2010/0298866 A1 | 11/2010 | Fischvogt |
| 2010/0305490 A1 | 12/2010 | Coulthard |
| 2010/0305524 A1 | 12/2010 | Vess et al. |
| 2010/0312575 A1 | 12/2010 | Witt |
| 2010/0318043 A1 | 12/2010 | Malhi et al. |
| 2010/0324510 A1 | 12/2010 | Andresen et al. |
| 2010/0324516 A1 | 12/2010 | Braga et al. |
| 2010/0325864 A1 | 12/2010 | Briones et al. |
| 2010/0331797 A1 | 12/2010 | Patel ET AL. |
| 2011/0004171 A1 | 1/2011 | Blott et al. |
| 2011/0004172 A1 | 1/2011 | Eckstein et al. |
| 2011/0008179 A1 | 1/2011 | Turner et al. |
| 2011/0009835 A1 | 1/2011 | Blott |
| 2011/0009838 A1 | 1/2011 | Greener |
| 2011/0015593 A1 | 1/2011 | Svedman |
| 2011/0028918 A1 | 2/2011 | Hartwell |
| 2011/0028921 A1 | 2/2011 | Hartwell |
| 2011/0034892 A1 | 2/2011 | Buan |
| 2011/0046584 A1 | 2/2011 | Haggstrom |
| 2011/0054421 A1 | 3/2011 | Hartwell |
| 2011/0054422 A1 | 3/2011 | Locke et al. |
| 2011/0054423 A1 | 3/2011 | Blott et al. |
| 2011/0071483 A1 | 3/2011 | Gordon et al. |
| 2011/0077605 A1 | 3/2011 | Karpowicz et al. |
| 2011/0087176 A2 | 4/2011 | Blott |
| 2011/0087178 A2 | 4/2011 | Weston |
| 2011/0087180 A2 | 4/2011 | Weston |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0130712 A1 | 6/2011 | Topaz |
| 2011/0172615 A2 | 7/2011 | Greener et al. |
| 2011/0190735 A1 | 8/2011 | Locke et al. |
| 2011/0202220 A1 | 8/2011 | Seta et al. |
| 2011/0230849 A1 | 9/2011 | Coulthard et al. |
| 2011/0251567 A1 | 10/2011 | Blott et al. |
| 2011/0257572 A1 | 10/2011 | Locke et al. |
| 2011/0275964 A1 | 11/2011 | Greener |
| 2011/0282309 A1 | 11/2011 | Adie et al. |
| 2012/0001762 A1 | 1/2012 | Turner et al. |
| 2012/0053538 A1 | 3/2012 | Blott et al. |
| 2012/0078539 A1 | 3/2012 | Vernon-Harcourt et al. |
| 2012/0109084 A1 | 5/2012 | Blott et al. |
| 2012/0130325 A1 | 5/2012 | Blott et al. |
| 2012/0136325 A1 | 5/2012 | Allen |
| 2012/0157942 A1 | 6/2012 | Weston |
| 2012/0165764 A1 | 6/2012 | Allen et al. |
| 2012/0197229 A1 | 8/2012 | Buan |
| 2012/0302975 A1 | 11/2012 | Buan et al. |
| 2012/0302978 A1 | 11/2012 | Buan et al. |
| 2013/0018338 A1 | 1/2013 | Weston et al. |
| 2013/0110058 A1 | 5/2013 | Adie et al. |
| 2013/0150813 A1 | 6/2013 | Gordon et al. |
| 2013/0150814 A1 | 6/2013 | Buan |
| 2013/0296816 A1 | 11/2013 | Greener |
| 2013/0331823 A1 | 12/2013 | Askem et al. |
| 2014/0018753 A1 | 1/2014 | Joshi et al. |
| 2014/0088528 A1 | 3/2014 | Hartwell |
| 2014/0107599 A1 | 4/2014 | Fink et al. |
| 2014/0121617 A1 | 5/2014 | Locke et al. |
| 2014/0163494 A1 | 6/2014 | Buan et al. |

(56) References Cited

U.S. PATENT DOCUMENTS

| | | |
|---|---|---|
| 2014/0257212 A1 | 9/2014 | Boynton et al. |
| 2014/0316356 A1 | 10/2014 | Nicolini |
| 2015/0025482 A1 | 1/2015 | Begin et al. |

FOREIGN PATENT DOCUMENTS

| | | | |
|---|---|---|---|
| CA | 2390513 | A1 | 5/2001 |
| CA | 2121688 | C | 7/2001 |
| CA | 2408305 | | 11/2001 |
| CA | 2458285 | | 3/2003 |
| CA | 2157772 | C | 9/2003 |
| DE | 2809828 | | 9/1978 |
| DE | 3 935 818 | | 5/1991 |
| DE | 4 012 232 | | 10/1991 |
| DE | 198 44 355 | | 4/2000 |
| EP | 0 020 662 | | 7/1984 |
| EP | 0 355 186 | | 2/1990 |
| EP | 0 777 504 | | 10/1998 |
| EP | 0 782 421 | | 7/1999 |
| EP | 1 897 569 | | 8/2002 |
| EP | 0 708 620 | | 5/2003 |
| EP | 1 088 569 | | 8/2003 |
| EP | 1 440 667 | | 3/2006 |
| EP | 1 284 777 | | 4/2006 |
| EP | 1 171 065 | | 3/2007 |
| EP | 1 476 217 | | 3/2008 |
| EP | 1 121 163 | | 11/2008 |
| EP | 2098257 | A1 | 9/2009 |
| FR | 1163907 | | 10/1958 |
| GB | 114754 | | 4/1918 |
| GB | 641061 | | 8/1950 |
| GB | 1224009 | A | 3/1971 |
| GB | 1549756 | A | 8/1979 |
| GB | 2195255 | A | 4/1988 |
| GB | 2378392 | A | 2/2003 |
| GB | 2415908 | A | 1/2006 |
| JP | 2003-165843 | | 6/2003 |
| JP | 2010-504805 | | 2/2010 |
| JP | 2002-517288 | | 6/2010 |
| JP | 2010-531698 | | 9/2010 |
| SU | 1251912 | A1 | 4/1983 |
| WO | WO 1984/01904 | | 5/1984 |
| WO | WO 1990/11795 | | 10/1990 |
| WO | WO 1991/00718 | | 1/1991 |
| WO | WO 1992/20299 | | 11/1992 |
| WO | WO 1996/05873 | | 2/1996 |
| WO | WO 1998/19068 | | 5/1998 |
| WO | WO 1999/01173 | | 1/1999 |
| WO | WO 1999/064091 | | 12/1999 |
| WO | WO 2000/07653 | | 2/2000 |
| WO | WO 2000/50143 | A | 8/2000 |
| WO | WO 2000/59424 | | 10/2000 |
| WO | WO 2001/19430 | A1 | 3/2001 |
| WO | WO 01/037922 | | 5/2001 |
| WO | WO 2001/34223 | | 5/2001 |
| WO | WO 2001/85248 | | 11/2001 |
| WO | WO 01/93793 | | 12/2001 |
| WO | WO 2002/083046 | A1 | 10/2002 |
| WO | WO 2002/092783 | | 11/2002 |
| WO | WO 03/045492 | | 6/2003 |
| WO | WO 03/057307 | | 7/2003 |
| WO | WO 2003/092620 | | 11/2003 |
| WO | WO 2004/024300 | | 3/2004 |
| WO | WO 2004/037334 | | 5/2004 |
| WO | WO 2005/025666 | | 3/2005 |
| WO | WO 2005/051461 | | 6/2005 |
| WO | WO 2005/070480 | | 8/2005 |
| WO | WO 2005/082435 | | 9/2005 |
| WO | WO 2006/046060 | | 5/2006 |
| WO | WO 2008/049026 | | 10/2006 |
| WO | WO 07/030601 | | 3/2007 |
| WO | WO 2007/024230 | | 3/2007 |
| WO | WO 2007/087811 | | 8/2007 |
| WO | WO 2008/039223 | | 4/2008 |
| WO | WO 2008/048481 | | 4/2008 |
| WO | WO 2008/100440 | | 8/2008 |
| WO | WO 2008/135997 | | 11/2008 |
| WO | WO 2009/004291 | | 1/2009 |
| WO | WO 2009/004371 | | 1/2009 |
| WO | WO 2009/019415 | | 2/2009 |
| WO | WO 2009/047524 | | 4/2009 |
| WO | WO 09/066105 | | 5/2009 |
| WO | WO 09/066106 | | 5/2009 |
| WO | WO 2009/089390 | | 7/2009 |
| WO | WO 2010/039481 | | 4/2010 |
| WO | WO 2010/051418 | | 5/2010 |
| WO | WO 2010/093753 | | 8/2010 |
| WO | WO 2010/121186 | | 10/2010 |
| WO | WO 2010/126444 | | 11/2010 |
| WO | WO 2011/023275 | | 3/2011 |
| WO | WO 2011/087871 | | 10/2011 |
| WO | WO 2012/022484 | | 2/2012 |
| WO | WO 2012/162370 | | 11/2012 |
| WO | WO 2012/162382 | | 11/2012 |
| WO | WO 2012/038724 | | 3/2013 |
| WO | WO 2013/140255 | | 9/2013 |
| WO | WO 2013/171585 | | 11/2013 |
| WO | WO 2014/151930 | | 9/2014 |

OTHER PUBLICATIONS

Written Opinion of the International Searching Authority dated Sep. 6, 2012 in International Application No. PCT/US2012/039103 in 7 pages.
International Search Report dated Sep. 6, 2012 in International Application No. PCT/US2012/039103 in 3 pages.
U.S. Appl. No. 10/599,720, filed Oct. 6, 2006, Blott et al.
U.S. Appl. No. 12/192,000, filed Aug. 14, 2008, Hartwell et al.
U.S. Appl. No. 14/598,083, filed Jan. 15, 2015, Allen et al.
U.S. Appl. No. 60/559,727, filed Apr. 5, 2004, Weston.
U.S. Appl. No. 60/573,655, filed May 21, 2004, Weston.
European Extended Search Report, re EP Application No. 12789546.4, dated Dec. 5, 2014.
International Search Report dated Sep. 6, 2012 in International Application No. PCT/US2012/39103.
International Preliminary Report on Patentability dated Nov. 26, 2013 in International Application No. PCT/US2012/39103.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., Treatment of the Perinea! Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Biblehimer, Helen L., "Dealing With a Wound that Drains 1.5 Liters a Day," RN, Aug. 1986, pp. 21-23, USA.
Bier, A., Hyperemia as a Therapeutic Agent, *Ed. Dr. Gustavus M. Blech, A. Robertson & Co.*, Chicago 1905, pp. 74-85.
Brubacher, "To Heal A Draining Wound", RN Mar. 1982, 7 pages.
Bucalo et al. "Inhibition of Cell Proliferation by Chronic Wound Fluid." Wound Repair and Regeneration, Miami, 1993, pp. 181-186.
Canadian Office Action for Canadian Application No. 2739605 dated Aug. 22, 2011 in 2 pages.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chinese Office Action dated Aug. 29, 2008 for Patent Application No. 200480032101.1,
Chintamani, et al., "Half versus full vacuum suction drainage after modified radical mastectomy for breast cancer—a prospective randomized clinical trial", Research Article (Jan. 27, 2005), 1-5.
Costunchenok, BM, Effect of Vacuum on Surgical Purulent Wounds, Vestnik Chirurgia, 1986, 6 pages.

(56) References Cited

OTHER PUBLICATIONS

Davydov et al. "Pathogenic Mechanisms of the Effect of Vacuum Therapy on the Course of the Wound Process" pp. 43-46 (Dec. 1990).

Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik KhirurQii, BlueSky PublishinQ, La Costa, California (2004), 15-17.

Davydov, Yu A., et al., "The Bacteriological and Cytological Assessment of Vacuum Therapy of Purulent Wounds", The Kremlin Papers: Perspectives in Wound Care, Russian Journal: Vestnik KhirurQii, BlueSky PublishinQ, La Costa, California (2004), 11-14.

Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004\, 5-7.

De Lange, M.Y., et al., "Vacuum-Assisted Closure: Indications and Clinical Experience", Eur J Plast Surg (2000) 2;178-182 (Feb. 9, 2000).

Dilmaghani et al., "A Method for Closed Irrigation and Suction Therapy in Deep Wound Infections," Journal of Bone and Joint Surgery, 1969, vol. 51-A, No. 2, pp. 323-342.

EPO, Office Action for EP App. No. 04 791 592.1 dated Jun. 12, 2008.

EPO, Second European Office Action for EP App. No. 04 791 592.1 dated Feb. 10, 2011.

Fleischmann, Vacuum sealing: indication, technique, and results, European Journal of Orthopaedic Surgery & Traumatology (1995), pp. 37-40.

Fleischmann, W. Wund Forum Spezial. IHW '94. "Vakuumversiegelung zur Behandlung von Problemwuden" (with English translation: Vacuum Sealing for Treatment of Problematical Wounds).

Garcia-Rinaldi, R., et al., Improving the Efficiency of Wound Drainage Catheters, Amer. Journ. of Surg., Sep. 1975, pp. 130, 372-373.

Hartz, R.S., et al., Healing of the Perinea! Wound, Arch. Surg., Apr. 1980, 115, 471-474.

Health Technology, Literature R., "Vacuum Assisted Closure Therapy for Wound Care", Health Technology Literature Review (Dec. 2004), 3-59.

International Preliminary Report for International Application No. PCT/GB/2004/004549, dated Dec. 20, 2005.

International Search Report for International Application No. PCT/GB/2004/004549, dated Feb. 21, 2005.

Japanese Office Action dated Aug. 25, 2009 for Patent Application No. 2006-537411.

Japanese Office Action dated Dec. 15, 2009 for Patent Application No. 2006-537411.

Japanese Office Action dated Jun. 22, 2010 for Patent Application No. 2006-537411.

Japanese Office Action dated Jan. 17, 2012 for Patent Application No. 2010-59188.

Jeter, K.F., et al, "Managing Draining Wounds and Fistulae: New and Established Methods", Chronic Wound Care, pp. 240-246.

Johnson, F.E., An Improved Technique for Skin Graft Placement using a Suction Drain, Surgery, Gynecology and Obstetrics, Dec. 1984, 3 pages.

KCI Inc., If It's Not VAC Therapy, It's Not Negative Pressure Wound Therapy, Jan. 2005.

Khirugii, Vestnik, "A Collection of Published Studies Complementing the Research and Innovation of Wound Care", The Kremlin Papers, Perspectives in Wound Care, Russian Medical Journal, Vestnik Khiruqii, Blue Sky Publishing (2004), 2-17.

Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.

Landes, R.R. and I. Melnick, An Improved Suction Device for Draining Wounds, Arch. Surg., May 1972, 104, p. 707.

Linden, Willem van der, et al, "Randomized Trial of Drainage After Cholecystectomy: Suction Versus Static Drainage Through a Main Wound Versus a Stab Incision", American Journal of Surgery, Feb. 1981, vol. 141, oo. 289-294.

Mcfarlane, R.M., The Use of Continuous Suction under Skin Flaps, Br. Journ. Plast. Surg., pp. 77-86.

Mclaughlan, J, et al, "Sterile Microenvironment for Postoperative Wound Care", The Lancet, Sep. 2, 1978, pp. 503-504.

Meyer, W. and V. Schmeiden, Bier's Hyperemic Treatment, Published 1908 W. B. Saunders Company, pp. 44-65.

Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).

Nakayama, Y, et al, "A New Method for the Dressing of Free Skin Grafts", Plastic and Reconstructive Surgery, Dec. 1990 pp. 1216-1219, UK.

NURSING75, Wound Suction: Better Drainage with Fewer Problems, Nursing, vol. 5, No. 10, Oct. 1975, pp. 52-55.

Office Action (Final) for U.S. Appl. No. 10/575,875, published as 2007/129,707, dated Jun. 17, 2009 in 19 pages.

Ramirez, O.M., et al., Optimal Wound Healing under Op-Site Dressing, Ideas and Innovations, 73(3), pp. 474-475.

Ranson, J. H. C., et al, "Safer Intraperitoneal Sump Drainage", Surgery, Gynecology & Obstetrics, Nov. 1973, vol. 137, pp. 841-842.

Sames, C.P., Sealing of Wounds with Vacuum Drainage, Br. Med. Journ., Nov. 5, 1977, p. 1223, Correspondence.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Solovev, V.A. "Treatment and Prevention of Suture Failures after Gastric Resection" (Dissertation Abstract) (S.M. Kirov Gorky State Medical Institute, Gorky USSR 1988).

Stewart, Joanne, Ph.D., World Wide Wounds—Next generation of products for wound management—2002 (13 pages).

Svedman, P., "Irrigation Treatment in Split-Thickness Skin Grafting of Intractable Leg Ulcers," Scand J. Plast. Reconst. Surg., 19:211-213, 1985.

Svedman, P., "Irrigation Treatment of Leg Ulcers," The Lancet, Sep. 1983, 532-34.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swift, et al, "Quorum Sensing in *Aeromonas hydrophila* and *Aeromonas salmoncida*: Identification of LuxRI Homologs AhyRI and AsaRl and Their Cognate N-Acylhomoserine Lactone Signal Molecules," J. Bacterial., 179(17):5271-5281 (1997).

Teder and Svedman et al., "Continuous Wound Irrigation in the Pig," Journal of Investigative Surgery, 1990, vol. 3, pp. 399-407.

Tribble, David E. M.D., An Improved Sump Drain-Irrigation Device of Simple Construction, Archives of Surgery New York, pp. 511-13, 1972 vol. 105.

Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.

Venturi, Mark L., "Mechanisms and Clinical Applications of the Vacuum-Assisted Closure (VAC) Device", Am J Clin Dermatol (2005) 693, 185-194; Review Article (2005),185-194.

Vijanto, J. and J. Raekallio, Local Hyperalimentation of Open Wounds, Br. J. surg., 1976, 63, 427-430.

Wackenfors, A., et al., Effects of Vacuum-Assisted Closure Therapy on Inguinal Wound Edge Microvascular Blood Flow, *Wound Rep. Reg*, 2004, 12, 600-606.

Webb, New Techniques in Wound Management: Vacuum-Assisted Wound Closure, Journal of the American Academy of Orthopaedic Surgeons, v. 10, No. 5, pp. 303-311, Sep. 2002.

(56) References Cited

OTHER PUBLICATIONS

Webster's Revised Unabridged Dictionary, published 1913 by C. & G. Merriam Co., definition of Flapper Valve, downloaded from Free Online Dictionary.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Wu, W.S., et al. Vacuum therapy as an intermediate phase in would closure: a clinical experience, Eur J Plast Surg (2000) 23: pp. 174-177.
Office Action dated Jul. 17, 2015 received in Chinese Application No. 201280036812.0.
Meyer, D. et al., "Weight-Loaded Syringes as a Simple and Cheap Alternative to Pumps for Vacuum-Enhanced Wound Healing", Plastic and Reconstructive Surg., Jun. 2005, 2174-2176.

* cited by examiner

METHOD FOR PROVIDING NEGATIVE PRESSURE TO A NEGATIVE PRESSURE WOUND THERAPY BANDAGE

CROSS REFERENCE TO RELATED APPLICATIONS

This application is a continuation of U.S. patent application Ser. No. 13/299,783, filed Nov. 18, 2011, titled "METHOD FOR PROVIDING NEGATIVE PRESSURE TO A NEGATIVE PRESSURE WOUND THERAPY BANDAGE," which claims priority to U.S. Provisional Application No. 61/490,118, filed May 26, 2011, titled "METHOD FOR PROVIDING NEGATIVE PRESSURE TO A NEGATIVE PRESSURE WOUND THERAPY BANDAGE." The disclosure of each of these prior applications is hereby incorporated by reference in its entirety herein.

FIELD OF THE INVENTION

The invention relates to a method for providing negative pressure to a negative pressure wound therapy bandage.

BACKGROUND OF THE INVENTION

Negative pressure wound therapy is one method that is used to treat certain wounds or sores on people. In general the treatment includes, a bandage being placed over a wound site, and connected to a pumping device. The pumping device provides suction, creating a negative pressure under the bandage at the wound site. Exudates and other materials are removed from the wound site, allowing the wound to heal faster than under ambient pressure.

The pumping device includes, amongst other things, a pump. Typically, a user selects (or otherwise enters) an appropriate therapeutic pressure on the pumping device that correlates to the specific negative pressure treatment for that patient. It is important that the pump and pumping device achieve the therapeutic pressure that is to be used in association with the negative pressure wound therapy quickly and correctly.

The speed at which the pump can achieve the therapeutic pressure is important because the speed can detrimentally effect the treatment. Moreover, the ability for the pump to recognize that the therapeutic pressure has been achieved is important to avoid applying too little or too much negative pressure. Thus, for a pump device, the speed and the accuracy at which it obtains the therapeutic pressure is an important characteristic.

In order to accurately and quickly achieve the therapeutic pressure, some pumps are left on continuously. In some devices this can be problematic. For example, some pumps can quickly achieve the therapeutic pressure; however, the pump and system tends to overshoot the therapeutic pressure value. This requires additional valves and other components that allow the pumping device to release negative pressure until the appropriate negative pressure is obtained.

Moreover, leaving the pump on continuously can act as a power drain, and for pumping devices that operate on batteries or other portable power sources, this can negatively impact the life time of the power source.

The present invention is directed to resolving these and other matters.

SUMMARY OF THE INVENTION

In one embodiment of the invention, the invention is directed towards a method for providing negative pressure to a negative pressure wound therapy bandage by providing a pumping device having a pump and setting a therapeutic negative pressure on the pumping device. The pumping device determines a target negative pressure associated with the therapeutic negative pressure and the target negative pressure is less than the therapeutic negative pressure (as discussed herein, "less than" means it is less negative, or a lower amount of a negative pressure, in other words, closer to zero). The pumping device is connected to a negative pressure wound therapy bandage. The target negative pressure is achieved by cycling the pump on and off to create a negative pressure in the negative pressure wound therapy bandage, obtaining a plurality of samples of the negative pressure in the negative pressure wound therapy bandage, each sample being obtained at a first set time interval, calculating an average of a predetermined number of consecutive samples, comparing the average to the target negative pressure, and, continuing to cycle the pump on and off until the average is greater than the target pressure.

The method may also include after cycling the pump on and off until the average of samples is greater than the target pressure after the complete off cycle, sampling the negative pressure in the negative pressure wound therapy bandage at a second set time interval greater than the first set time interval.

In another embodiment of the invention, the sampling of the negative pressure in the negative pressure wound therapy bandage at the second set time interval begins when the pump has been off for a predetermined amount of time.

The predetermined amount of time may be 300 milliseconds.

The second set time interval may be 1000 milliseconds and the first set time interval is 100 milliseconds.

In an embodiment, the cycling of the pump on and off to create negative pressure in the negative pressure wound therapy bandage on is performed by turning the pump on for 80 milliseconds and then turning the pump off for 80 milliseconds.

In some embodiments of the present invention, the therapeutic negative pressure is 125 mmHg and the target negative pressure is approximately 115 mmHg.

In some embodiments of the present invention, the therapeutic negative pressure is 90 mmHg and the target negative pressure is approximately 85 mmHg.

In some embodiments of the present invention, the therapeutic negative pressure is 60 mmHg and the target negative pressure is approximately 54 mmHg.

In some embodiments of the present invention, the therapeutic negative pressure is 40 mmHg and the target negative pressure is approximately 34 mmHg.

In another embodiment of the invention, the invention is for a method for providing negative pressure to a negative pressure wound therapy bandage by providing a pumping device having a pump and setting a therapeutic negative pressure on the pumping device. The pumping device determines a target negative pressure associated with the therapeutic negative pressure and the target negative pressure is less than the therapeutic negative pressure. The pumping device is connected to a negative pressure wound therapy bandage. The target negative pressure is achieved by cycling the pump on and off for a first predetermined amount of time to create a negative pressure in the negative pressure wound therapy bandage, obtaining a plurality of samples of the negative pressure in the negative pressure wound therapy bandage, each sample being obtained at a first set time interval, calculating an average of a predetermined number of consecutive samples, comparing the average to the target negative pressure, and, if the average is not greater than the target negative pressure, repeating the steps of cycling the pump on and off, obtaining a plurality of samples, calculating an average and comparing the average, until the average is greater than the target negative pressure.

In some embodiments the comparing of the average occurs at a rate faster than the rate of calculating the average.

In some embodiments, if the average is greater than the target negative pressure, the target negative pressure is maintained by obtaining a plurality of second samples of the negative pressure in the negative pressure wound therapy bandage at a second set time interval begin greater than the first time interval, and, comparing each second sample to the target negative pressure, and, repeating the steps of obtaining and comparing if a second sample is greater than the target negative pressure.

In some embodiments, if a second sample is not greater than the target negative pressure, the step of achieving the target negative pressure by: cycling the pump on and off; obtaining a plurality of samples; calculating an average; and, comparing the average until the average is greater than the target negative pressure, is repeated.

In the various embodiments of the present invention, the therapeutic negative pressure may be selected from the group consisting of: 40 mmHg; 60 mmHg; 90 mmHg; and, 125 mmHg.

An invention according to one or more of the disclosed embodiments allows the pump to achieve the therapeutic negative pressure/target negative pressure reasonably quickly and limit exceeding the therapeutic negative pressure/target negative pressure as much as practical.

Moreover, at least one of the embodiments also provides a reliable method to detect when the bandage pressure was being "topped-up" too frequently due to a leak (i.e., often returning to cycle the pump on and off to increase negative pressure). It is expected that the system will leak a small amount over time, for example, due to the imperfect plumbing connections in the system. A leak rate of one "top-up" per minute is normal. However, a leak rate four times that is cause for a minor leak to be declared. Such a leak rate is still within the bounds of the system to handle long term but the user should be informed so that it is corrected and system battery life is extended. It is also desirable to clear the fault as soon as it appears that the leaking has returned to normal levels.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The present invention will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings as provided below.

DETAILED DESCRIPTION OF THE DRAWINGS

Figure 1:
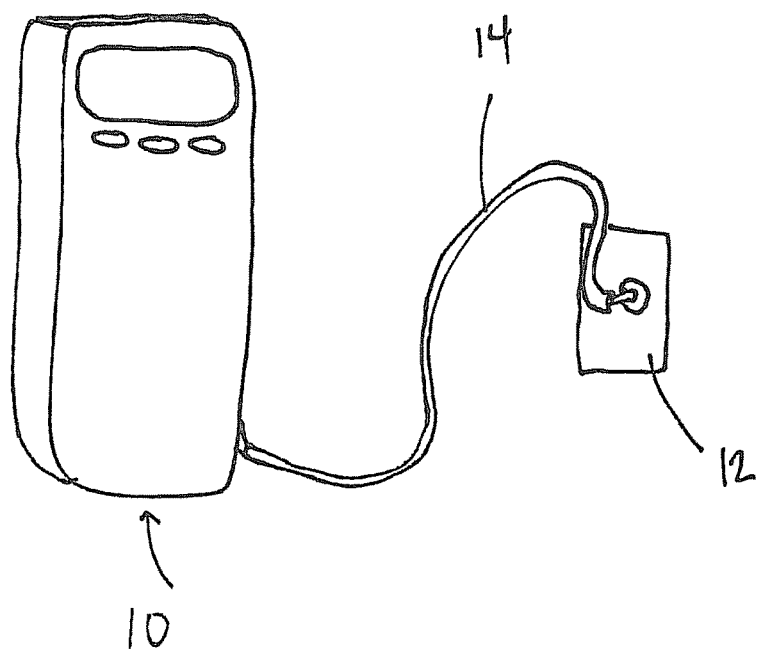
FIG. 1 is a front perspective view of a device used in association with one or more embodiments of the present invention.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Reference throughout this description to features, advantages, objects or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Figure 2:
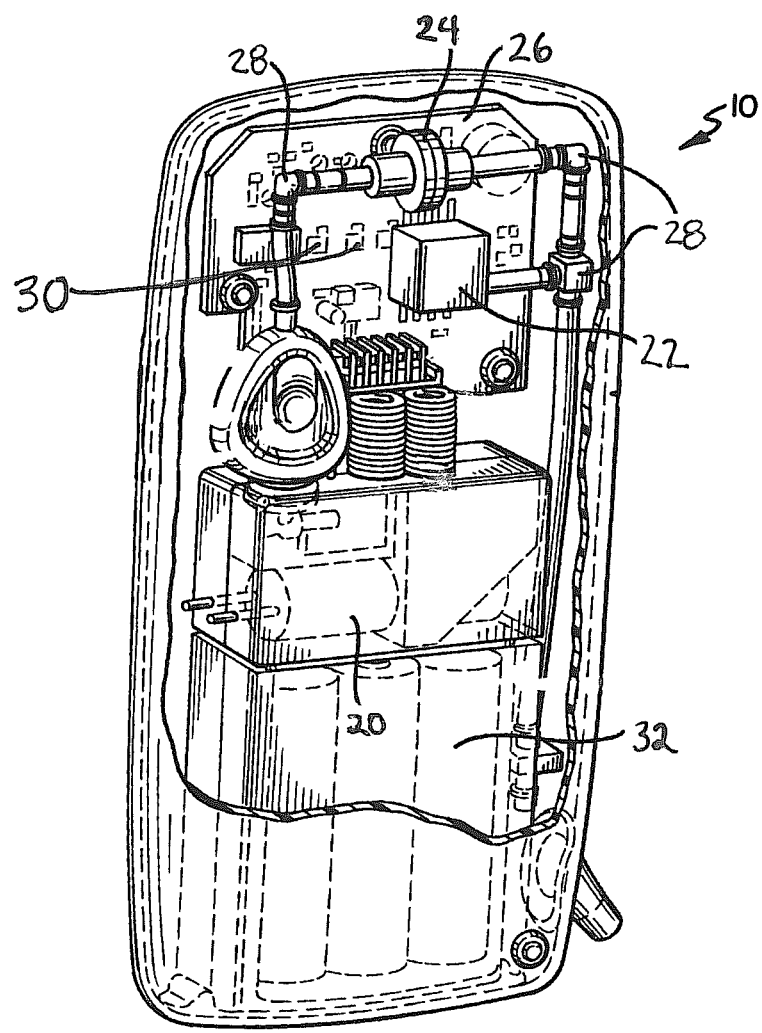
FIG. 2 is a front side cutaway view of a device provided according to one or more embodiments of the present invention.

As shown in the attached FIGS. 1 and 2, the present invention is directed towards a method used with a pumping device 10 having a pump 20. The pumping device 10 generally includes a pressure sensor 22, a check valve 24, a control circuit 26 (with microcontroller), internal plumbing 28, LEDs 30 and a power source 32.

In order to provide negative pressure to a wound, the pumping device 10 is connected to a negative pressure wound therapy bandage 12, typically with tubing 14.

In order to achieve a target negative pressure the pumping device 10 turns the pump 20 on for short amounts of time when the pressure is below the target pressure.

The pump device 10 typically operates as follows: a microcontroller turns the pump 20 on via a digital output; the pump 20 starts producing a vacuum; the vacuum is converted to a voltage by a pressure sensor 22; the voltage is converted by an analog to digital converter ("the A/D") to a standard, recognized pressure engineering unit; and, the microcontroller compares the monitored pressure to the target pressure.

In order to achieve the target negative pressure in a short amount of time and avoid overshooting the target negative pressure, the pump 20 is cycled. The duty cycle, the percentage of pump on time relative to pump off time, after examining several pumps in action, can be constant for a variety of pumps 20. How much vacuum the pump 20 can draw in a short time period will influence the pump on time. Moreover, bandage 14 and plumbing 28 elasticity and how quickly the pressure sensor 22 and the A/D can take a measurement will influence the pump off time.

In one embodiment, the pressure sensor 22 measurement time is 20 milliseconds; while the A/D measurement time is 16 microseconds. Therefore, since a change in pressure must first be converted by the pressure sensor 22 and then the A/D, the minimum measurement time is 20.016 milliseconds.

It is believed to be advantageous to average readings before they are used to mitigate occasional measurement system anomalies. The number of samples in the average, on the one hand, when it tends to be low, do some anomaly mitigation but also remain the most responsive to quick changes in the parameter they are measuring. The best anomaly mitigation appears to occur when the number of samples is high, but then the averaging is not very responsive to quick changes in the parameter they are measuring.

It was determined that it would be advantageous to use a sliding 5 sample average. If the pressure were sampled continuously, a complete average would be ready in: 5×20.016=100.090 milliseconds. However, it would not be necessary to wait for all 5 samples to be acquired before a pump control decision was made on the value because just a few samples still mitigates against system anomalies sufficiently. However, sampling the pressure continuously, especially since the pressure sensor 22 places the largest mA load of any component (other than the pump 20) on the system would unnecessarily shorten battery life for too little gain in pump control.

Consequently, a measurement process asynchronous to the pump on/off cycle was used wherein pressure samples are contributed to the average every 100 milliseconds, and if the pump on/off control logic compared the average every 80 milliseconds it would compare it often enough to determine an average affected by the very last contribution that was made to that average. This can be achieved by: starting the process every 100 milliseconds; waiting the 20 milliseconds pressure sensor measurement time; then, measuring the pressure with the A/D.

It is contemplated to synchronize the completion of the A/D measurement to the pump on/off control logic exactly but software design best practice says that dependencies between software modules should be avoided where possible and synchronization is not necessary here—the pump on/off control logic (cycle) will see every change any contribution makes to the average.

When the pump 20 has met its target pressure, the A/D sampling and comparing process detailed above changes from, for example, a repeat rate of 100 milliseconds to a repeat rate of 1000 milliseconds when the pump has been off for a sufficient amount of time. This further saves battery life at a time when the pressure is not likely to change very much. The period of time the pump 20 has to be off to switch to the slower repeat rate may be, for example, 300 milliseconds; however, it may be any value that was larger than the off period in the pump on/off duty cycle (more later on the duty cycle). Moreover, it should be at least that long to distinguish the "off" that is due to the pump 20 having reached the target pressure and the "off" of the pump control duty cycle. (The 300 milliseconds was utilized as it is a sufficient amount of time for the A/D to wait before it samples the battery voltage after the pump is turned off. The battery is only sampled when the pump 20 is turned off because the mA load that the pump places on the system is significantly different than when it is off and battery life is more easily predicted when the pump is not loading the system.)

The pump control on/off duty cycle is preferably 80 milliseconds on and 80 milliseconds off. It was determined that an "on" time of 40 or 80 milliseconds was sufficient for constraining the overshoot for a variety of bandages 12. The 40 milliseconds value constrained it better, yielded end pressures closer to the target pressure, but took longer to get to the target pressure. The "on" times longer than 80 milliseconds created out-of-bounds overshoot for some bandages—no matter what the "off" time was. As mentioned above, the "off" time has an effect on the measurement part of the control/measurement algorithm. Further, plumbing and bandage elasticity, although minor, can contort the average or "steady" pressure for a short while. It is believed that it is advantageous to let such pressure contortions settle before measurement. Moreover, the pressure sensor 22 and A/D measurements need time also as noted above.

An "off" time of approximately 30 milliseconds would cover both but it was convenient to use the same 80 milliseconds timer to control both the on time and the off time. Further, letting the system settle longer, for one or more multiples of the 80 milliseconds, would improve the quality of the measurement because it would let the sliding average fill more completely—at the cost of taking longer to get to the end pressure. While these times have been discussed, nothing herein should be construed to limit the present invention to these times.

In use, a user inputs the therapeutic negative pressure into the pumping device. Of course, this can be accomplished with the pumping device having pre-set therapeutic negative pressures and the user merely selects one.

In one or more embodiments of the present invention, a target negative pressure is set slightly less than the therapeutic negative pressure entered by the user into pumping device. In a working example of an embodiment of the invention, the following parameters were used with the object to obtain the therapeutic negative pressure of 40/60/90/125 mmHg within 15 seconds and limit overshoot to +/−10% of the therapeutic negative pressure. However, for the 40 mmHg therapeutic negative pressure, the tolerance is preferably +/−10 mmHg (not +/−10%).

Using a target negative pressure that is set slightly less than the 40/60/90/125 therapeutic negative pressure allows for compensation of the system's tendency to undervalue the actual negative pressure within the bandage. Therefore, the target pressures contemplated to be used with the previously mentioned therapeutic negative pressure values are 34, 54, 85 and 115 mmHg (respectively). Other target pressures can be used depending on the variety of parameters discussed above (pump, bandage, elasticity, etc.) without departing from the spirit of the present invention.

In a device according to one or more embodiments of the present invention, the pump 20 will reasonably quickly achieve the target negative pressure, stop, "top-up" once or twice after a few seconds and transition to the state where it only tops-up every minute or so to compensate for system leaking. The initial one or two top-ups are due to the pressure completely settling.

In sum, in one or more embodiments of the present invention, pressure is sampled every 100 ms; with the sampling by the pressure sensor and A/D taking 20.016 milliseconds. Samples go into a sliding 5 element average. The pumping device 10 asynchronously compares the average every 80 milliseconds s (slightly faster than the pressure is sampled). The pumping device 10 turns the pump 20 on for no more than one cycle (80 milliseconds) if pressure is below target pressure. After waiting one off cycle (80 milliseconds), if the pressure is still below the target pressure, the pump 20 is turned on again. These last two steps repeat until the pressure is greater than the target pressure, at which point the pump 20 is left off until the normal leaking in the system reduces the pressure below the target pressure. During the period when the pressure is above the target pressure, starting when the pump 20 has been continuously off for 300 milliseconds, sampling may be reduced to the 1000 milliseconds rate (to extend battery life).

Figure 3:
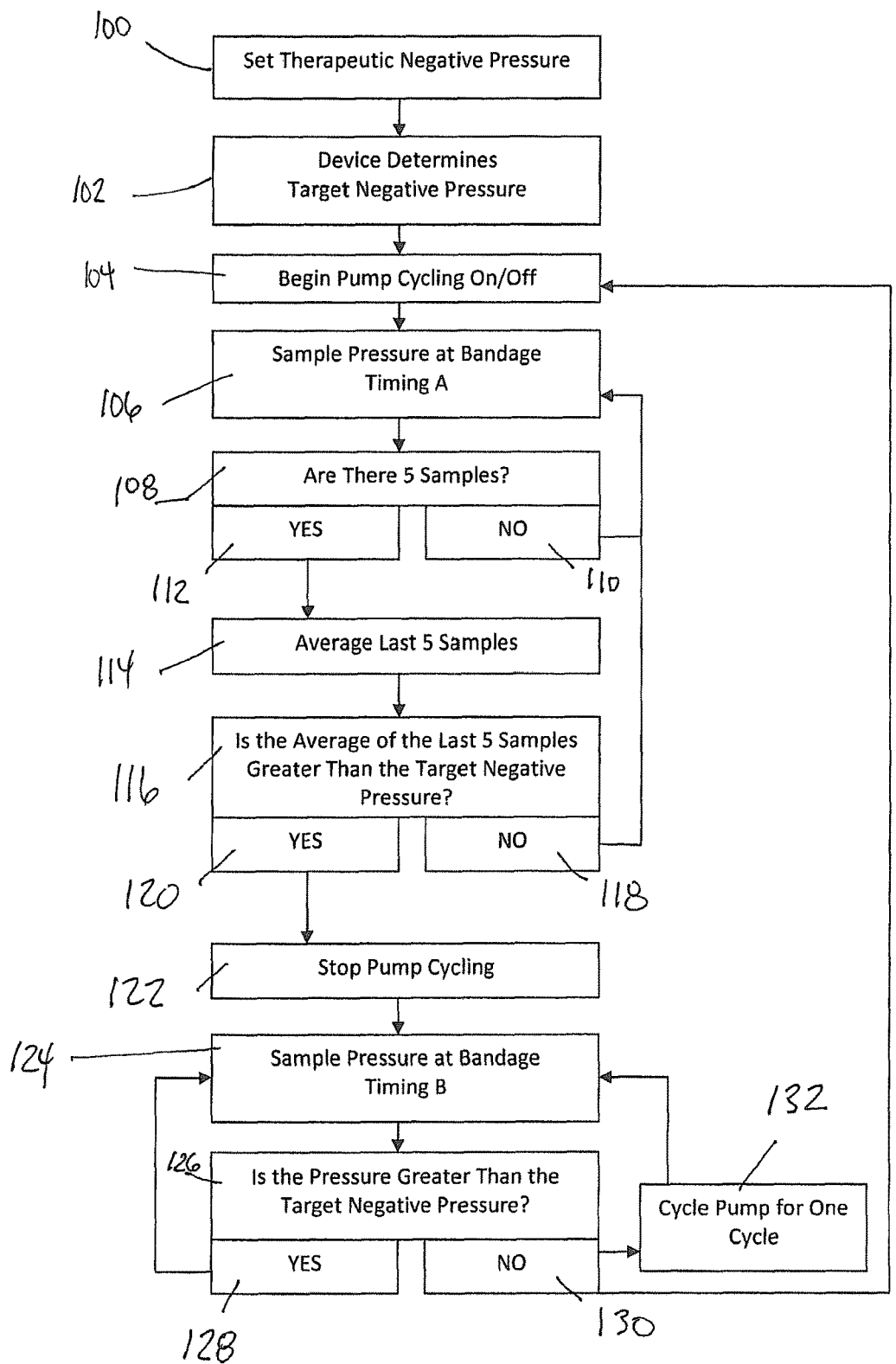
FIG. 3 is a flow chart of a method according to one or more embodiments of the present invention.

A flow chart for performing the steps of some embodiments is shown in FIG. 3. As shown therein, and as discussed above, a method according to one or more embodiments of the present invention may begin with the setting of a therapeutic negative pressure 100. In response to same, the pumping device will determine a target negative pressure 102. As previously discussed the target negative pressure is less than the therapeutic negative pressure.

At this point, the pumping device will begin to cycle the pump on and off 104. In addition, the pumping device will also begin sampling the pressure at the bandage 106. This sampling is preferably done at a set time. In FIG. 3, this is shown as being at "Timing A." The pumping device determines if there are at least five samples measured 108. If less than five samples have been collected 100, the pumping device continues to sample the pressure at the bandage 106.

If, however, more than five samples have been collected 112, the pumping device will calculate the average of the last five samples taken 114. The pumping device will then compare the average of the last five samples to the target negative pressure 116. If the average of the last five samples is less than the target negative pressure 118, the pumping device will continue to sample the pressure at the bandage 106.

If the average of the last five samples is greater than the target pressure 120, the pumping device will cease the pump cycling. It is contemplated, although not required, that if the pump is in the middle of a cycle, that specific cycle be completed, before the pumping cycling is stopped. Alternatively, the pump cycling can be immediately stopped when the average is determined to be greater than the target negative pressure.

After the pump cycling has been stopped, the device begins sampling the pressure at the bandage 124. This sampling is conducted, preferably at a predetermined time interval, and as shown, occurs at "Timing B." As previously mentioned, in order to increase the life of the batteries that may be powering the pumping device, it is preferred that Timing B is greater than Timing A.

Finally, the device continues to compare the sample of the pressure (taken in step 124) with the target negative pressure 126. If the most recent sample is greater than the target negative pressure 128, the device continues to sampling the pressure at the bandage 124.

If the most recent sample is less than the target pressure 130, the device may turn the pump on for one cycle 132, and continue to sample the pressure under the bandage 124. Alternatively, the device can return to cycling the pumping on and off 104 and the subsequent steps previously taken to achieve the target negative pressure.

In addition to achieving and maintaining negative pressure, one or more embodiments of the present invention also include a method for detecting a leak. For example, if the target negative pressure has been reached and at least 20 top-ups have occurred at the target negative pressure and the average of the last N (=3) top-up intervals is less than 15 seconds, a leak may be declared by the pump device. The minor leak detection may be cleared if the pump is disabled by the user or the top-up intervals are greater than or equal to 15 seconds.

The 15 seconds time value is related to an unacceptable leak rate (4 top-ups per minute) that was determined to be optimal. The pumping device records the time (since unit reset) of every top-up into a circular array of N elements and checks the top-up interval at every top-up or every 80 milliseconds, whichever occurs first. (The "or 80 milliseconds" facet is more useful for clearing the fault than declaring it.)

The time in the oldest of the array elements is subtracted from the current time and then divided by N to either yield the average of the last N top-ups (or what the average would have been if the 80 milliseconds timer tick that prompted the check was a top-up). An example of setting the fault and clearing the fault is given below:

TABLE ONE

Setting the fault
(assume 17 top-ups for this pressure have already occurred):

| Top-Up # | Time | Note |
| --- | --- | --- |
| 18 | 05:42:23.000 | |
| 19 | 05:42:33.000 | |
| 20 | 05:42:43.000 | Check called due to this top-up. System time is 05:42:43. System time − oldest top-up time = 00:00:20 00:00:20/3 = 6 6 < 15, fault declared |

The checks called due to the 80 milliseconds timer expiring are not shown in the above because they would have had no effect and their omission makes it easier to understand how the checks due to just the top-ups take place.

TABLE TWO

Clearing the fault (assume a continuation of the above TABLE ONE)

| Top-Up # | Time | Note |
| --- | --- | --- |
| 18 | 05:42:23.000 | |
| 19 | 05:42:33.000 | |
| 20 | 05:42:43.000 | Check called due to this top-up. System time is 05:42:43. System time-oldest top-up time = 00:00:20 00:00:20/3 = 6 6 < 15, fault declared |
| | 05:42:43.080 | Check called due to 80 ms timer tick, System time is 05:42:43.080 System time-oldest top-up time = 00:00:20.080 00:00:20.080/3 = 6 6 still less than 15, fault stands |
| | 05:42:43.160 | Similar to the previous, fault stands |
| | etc | No top-ups |
| | etc | No top-ups |
| | 05:43:08.000 | Check called due to 80 ms timer tick System time is 05:43:08.000 System time − oldest top-up time = 00:00:45 00:00:45/3 = 15 15 is not less than 15, fault cleared. |

In the example above, the fault was cleared within 25 seconds of the last top-up, a fraction of three times the 15 seconds threshold (the threshold used to declare the fault). This is consistent with the goal of clearing the fault quickly if it appears as though the fault has been corrected. It could have been cleared even sooner, as fast as within 15 seconds, if the system time was compared to the newest recorded top-up instead of the oldest—but using more than one top-up time gives greater confidence that the fault has really been cleared.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A method of providing negative pressure wound therapy comprising:

determining a therapeutic negative pressure for a negative pressure wound therapy device having a source of negative pressure, wherein the negative pressure wound therapy device is configured to be fluidically connected to a wound covered by a wound dressing;

attaining the therapeutic negative pressure under the wound dressing by activating the source of negative pressure, measuring wound pressure under the wound dressing at a first sampling rate, and determining based on the measured wound pressure that the therapeutic negative pressure is reached and thereafter deactivating the source of negative pressure; and maintaining the therapeutic negative pressure under the wound dressing by alternately activating and deactivating the source of negative pressure based on measuring the wound pressure under the wound dressing at a second sampling rate lower than the first sampling rate, the maintaining comprising activating the source of negative pressure in response to determining that the wound pressure is more positive than the therapeutic negative pressure and deactivating the source of negative pressure in response to determining that the wound pressure reaches the therapeutic negative pressure.

2. The method of claim 1, wherein maintaining the therapeutic negative pressure comprises keeping the pressure under the wound dressing within ±10% of the therapeutic negative pressure by alternately activating and deactivating the source of negative pressure.

3. The method of claim 1, wherein alternately activating and deactivating the source of negative pressure comprises one or more activations and one or more corresponding deactivations during a period of time, the period of time beginning when the source of negative pressure is first deactivated after the therapeutic negative pressure has been attained.

4. The method of claim 1, wherein attaining the therapeutic negative pressure under the wound dressing comprises activating the source of negative pressure until an average pressure under the wound dressing reaches the therapeutic negative pressure and thereafter deactivating the source of negative pressure, the average pressure being determined by:
measuring a plurality of pressures under the wound dressing, and
averaging the plurality of measured pressures.

5. The method of claim 4, wherein attaining the therapeutic negative pressure under the wound dressing comprises comparing the average pressure to the therapeutic negative pressure.

6. The method of claim 4, wherein maintaining the therapeutic negative pressure under the wound dressing comprises maintaining the average pressure under the wound dressing.

7. The method of claim 6, wherein maintaining the average pressure under the wound dressing comprises keeping the average pressure under the wound dressing within ±10% of the therapeutic negative pressure.

8. The method of claim 1, further comprising:
detecting a presence of a leak while maintaining the therapeutic negative pressure under the wound dressing by determining that the source of negative pressure has been activated more than a threshold number of activations over a time interval; and
indicating the presence of a detected leak with at least one of a visual indication, an audio indication, or deactivation of the source of negative pressure.

9. The method of claim 8, wherein the threshold number of activations is 20 activations.

10. The method of claim 1, further comprising:
detecting a presence of a leak when the source of negative pressure is activated for a threshold activation duration; and
indicating the presence of a detected leak with at least one of a visual indication, an audio indication, or deactivation of the source of negative pressure.

11. The method of claim 1, wherein the therapeutic negative pressure is configured to range from about −40 mmHg to about −125 mmHg.

12. A method of providing negative pressure wound therapy comprising:
determining a therapeutic negative pressure for a negative pressure wound therapy device having a source of negative pressure, wherein the negative pressure wound therapy device is configured to be fluidically connected to a wound covered by a wound dressing;
measuring a plurality of pressures under the wound dressing;
averaging the plurality of measured pressures;
activating the source of negative pressure, measuring wound pressure under the wound dressing at a first sampling rate, and determining based on the measured wound pressure that the average pressure under the dressing achieves the therapeutic negative pressure, and thereafter deactivating the source of negative pressure; and
maintaining the average pressure under the dressing to within ±10% of the therapeutic negative pressure by alternately activating and deactivating the source of negative pressure based on measuring the wound pressure under the wound dressing at a second sampling rate lower than the first sampling rate, the maintaining comprising activating the source of negative pressure in response to determining that the wound pressure is more positive than the therapeutic negative pressure and deactivating the source of negative pressure in response to determining that the wound pressure reaches the therapeutic negative pressure.

13. The method of claim 12, further comprising:
detecting a presence of a leak while maintaining the average pressure under the dressing by determining that the source of negative pressure has been activated more than a threshold number of activations over a time interval; and
indicating the presence of a detected leak with at least one of a visual indication, an audio indication, or deactivation of the source of negative pressure.

14. The method of claim 13, wherein the threshold number of activations is 20 activations.

15. The method of claim 12, further comprising:
detecting a presence of a leak when the source of negative pressure is activated for a threshold activation duration; and
indicating the presence of a detected leak with at least one of a visual indication, an audio indication, or deactivation of the source of negative pressure.

16. The method of claim 12, wherein the therapeutic negative pressure is configured to range from about −40 mmHg to about −125 mmHg.

17. A negative pressure wound therapy apparatus comprising:
a source of negative pressure configured to be fluidically connected to a wound covered by a wound dressing;

a pressure sensor configured to measure pressure under the wound dressing; and a controller configured to:

determine a therapeutic negative pressure for the source of negative pressure;

initially activate the source of negative pressure to attain the therapeutic negative pressure under the wound dressing, measure wound pressure under the wound dressing at a first sampling rate, determine based on the measured wound pressure that the therapeutic negative pressure has been reached, and subsequently deactivate the source of negative pressure when the therapeutic negative pressure under the wound dressing has been attained; and after therapeutic negative pressure under the wound dressing has been attained, maintain the therapeutic negative pressure under the wound dressing by alternately activating and deactivating the source of negative pressure based on measuring the wound pressure under the wound dressing at a second sampling rate lower than the first sampling rate, the controller further configured to activate the source of negative pressure in response to determining that the wound pressure is more positive than the therapeutic negative pressure and deactivating the source of negative pressure in response to determining that the wound pressure reaches the therapeutic negative pressure.

18. The apparatus of claim 17, wherein the controller is further configured to:

maintain the pressure under the dressing to within ±10% of the therapeutic negative pressure by alternately activating and deactivating the source of negative pressure.

19. The apparatus of claim 17, wherein the controller is further configured to:

calculate an average pressure under the dressing;

compare the average pressure to the therapeutic negative pressure; and initially activate the source of negative pressure and allow the source of negative pressure to be active until the average pressure under the dressing reaches the therapeutic negative pressure, and subsequently deactivate the source of negative pressure.

20. The apparatus of claim 19, wherein the controller is further configured to:

maintain the average pressure under the dressing to within ±10% of the therapeutic negative pressure by alternately activating and deactivating the source of negative pressure.

21. The apparatus of claim 17, wherein the controller is further configured to:

detect a presence of a leak while maintaining the therapeutic negative pressure under the dressing by determining that the source of negative pressure has been activated more than a threshold number of activations over a time interval; and indicate the presence of a detected leak with at least one of a visual indication, an audio indication, or deactivation of the source of negative pressure.

22. The apparatus of claim 21, wherein the threshold number of activations is 20 activations.

23. The apparatus of claim 17, wherein the controller is further configured to:

detect a presence of a leak when the source of negative pressure is activated for a threshold activation duration; and indicate the presence of a detected leak with at least one of a visual indication, an audio indication, or deactivation of the source of negative pressure.

24. The apparatus of claim 20, wherein the controller is further configured to:

detect a presence of a leak while maintaining the average pressure under the dressing by determining that the source of negative pressure has been activated more than a threshold number of activations over a time interval; and indicate the presence of a detected leak with at least one of a visual indication, an audio indication, or deactivation of the source of negative pressure.

25. The apparatus of claim 24, wherein the threshold number of activations is 20 activations.

26. The apparatus of claim 20, wherein the controller is further configured to:

detect a presence of a leak when the source of negative pressure is activated for a threshold activation duration; and indicate the presence of a detected leak with at least one of a visual indication, an audio indication, or deactivation of the source of negative pressure.

27. The apparatus of claim 17, wherein the therapeutic negative pressure is configured to range from about −40 mmHg to about −125 mmHg.

* * * * *